United States Patent [19]
Nickerson et al.

[11] Patent Number: 5,720,798
[45] Date of Patent: Feb. 24, 1998

[54] MICROMACHINED ANALYTE TRAP FOR GAS PHASE STREAMS

[75] Inventors: Mark A. Nickerson, Landenberg; W. Dale Snyder, West Chester, both of Pa.

[73] Assignee: Hewlett-Packard Company, Palo Alto, Calif.

[21] Appl. No.: 641,248

[22] Filed: Apr. 30, 1996

[51] Int. Cl.⁶ .................. B01D 15/08; B01D 53/04
[52] U.S. Cl. .................. 96/102; 96/105; 96/143; 96/154
[58] Field of Search .................. 96/101–108, 143, 96/145, 154; 95/100

[56] References Cited

U.S. PATENT DOCUMENTS

| | | | |
|---|---|---|---|
| 1,934,075 | 11/1933 | Lewis | 95/100 |
| 3,149,941 | 9/1964 | Barnitz et al. | 96/101 |
| 3,748,833 | 7/1973 | Karas et al. | 96/105 |
| 4,474,889 | 10/1984 | Terry et al. | 436/161 |
| 4,935,040 | 6/1990 | Goedert | 55/197 |
| 5,087,275 | 2/1992 | Pribat et al. | 96/101 |
| 5,116,495 | 5/1992 | Prohaska | 96/101 X |
| 5,151,110 | 9/1992 | Bein et al. | 96/101 X |
| 5,165,292 | 11/1992 | Prohaska | 96/102 X |
| 5,288,310 | 2/1994 | Peters et al. | 96/105 X |
| 5,522,918 | 6/1996 | Shiramizu | 96/143 X |

FOREIGN PATENT DOCUMENTS

| | | | |
|---|---|---|---|
| 60-142254 | 7/1985 | Japan | 96/101 |
| 60-229340 | 10/1985 | Japan | 96/101 |
| 60-229342 | 10/1985 | Japan | 96/101 |
| 61-142462 | 6/1986 | Japan | 96/101 |
| 61-155858 | 7/1986 | Japan | 96/101 |
| 61-176853 | 8/1986 | Japan | 96/101 |
| 61-233365 | 10/1986 | Japan | 96/101 |
| 61-233366 | 10/1986 | Japan | 96/101 |
| 61-288154 | 12/1986 | Japan | 96/101 |

OTHER PUBLICATIONS

S. Hagiwara, T. Shiina, Y. Takayama, E. Yano; Sord Computer Corporation; "Fabrication Gas Chromatography On A Silicon Wafer"; Periodical Title: Proceedings. IECON'84; Int'l Conf. on Industrial Electron, 1984, pp. 769–775.

S. Terry, J. Jerman, J. Angell, Stanford Electronic Laboratories, Stanford University, Stanford, CA; "A Gas Chromatographic Air Analyzer Fabricated On A Silicon Wafer"; IEEE Transactions On Electron Devices, vol. ED–26, No. 12, Dec. 1979, pp. 1880–1886.

*Primary Examiner*—Robert Spitzer
*Attorney, Agent, or Firm*—Richard F. Schuette

[57] ABSTRACT

A method and apparatus for non-liquid solvent introduction of analyte into an analytical instrument and, more particularly, to a bonded liquid phase analyte trap with integral flow switching that may include a rapid solid-state heating and cooling device. The analyte trap includes a first wafer having a flow channel formed on its bottom side such that a second wafer attached to the bottom side of the first wafer encloses the flow channel and a stationary phase coating is chemically bonded to the walls of the flow channel to provide a mechanism for trapping analytes of interest.

7 Claims, 4 Drawing Sheets

MICROMACHINED ANALYTE TRAP FOR GAS PHASE STREAMS

FIELD OF THE INVENTION

The present invention relates to methods and apparatus for non-liquid solvent introduction of analyte into the injection port of a gas chromatograph and, more particularly, to a micromachined silicon device that provides a bonded liquid phase analyte trap with integral flow switching and a means for rapid solid-state heating and cooling.

BACKGROUND OF THE INVENTION

Many techniques exist for the introduction of analytes into the injection port of a gas chromatograph. Injection by syringe is the most popular technique, however, it typically requires the use of a liquid solvent and may require a complicated mechanism for automation. Alternative analyte introduction techniques such as headspace and thermal desorption are slow, bulky and not ideally suited for small sample sizes or possible implementation with a micromachined gas chromatograph.

Solid phase microextraction is a relatively new technique disclosed in International Application Number PCT/CA91/00108 entitled "Method and Device for Solid Phase Microextraction and Desorption" by Janusz B. Pawliszyn, that provides for faster analyte introduction, but has many limitations relating to sample capacity, broad sample volatility, desorption time and retention time. A solid fused silica fiber coated with a secondary phase is attached to a plunger mechanism of a standard syringe such that the fiber can be extended from the inside hollow syringe needle into a vial containing analytes of interest. The analytes of interest then diffuse into the stationary phase coating until equilibrium is reached. The fibre is then withdrawn and inserted into the injection port of a gas chromatograph such that the analytes of interest may be thermally desorbed. A thick coating of stationary phase on the fibre (50–100 um) results in increased sample capacity, however, volatile analytes of interest become trapped with semivolatiles. Thus, it takes longer to desorb and results in a high bleed based on monomers and breakdown products from the stationary phase arriving at the detector. A thin coating reduces bleed and the time required for desorption, however, more volatiles are lost in favor of semivolatiles such that overall sample capacity is reduced.

The article entitled "Use of Open-Tubular Trapping Columns for On-Line Extraction-Capillary Gas Chromatography of Aqueous Sample" describes the solvent based chemistry involved with the extraction of analytes of interest involving the sorption of analytes from water into the stationary phase coating of an open-tubular column, removal of the water by purging the trap with nitrogen, and desorption of the analytes of interest with an organic solvent. The effect of swelling of the stationary phase with organic solvents on the retention power of the trap is also described.

There exists a need for a precise, rapid, compact, inexpensive, non-liquid solvent technique for introducing a sample into the injection port of a gas chromatograph.

A need also exists to introduce only analytes of interest onto the head of a column coupled to the injection port.

SUMMARY OF THE INVENTION

The invention provides a method and apparatus for non-liquid solvent introduction of analyte into an analytical instrument and, more particularly, to a bonded liquid phase analyte trap with integral flow switching that may include a means for rapid solid-state heating and cooling.

The analyte trap comprises a first wafer having a flow channel formed on its bottom side such that a second wafer attached to the bottom side of the first wafer encloses the flow channel. A stationary phase coating is chemically bonded to the walls of the flow channel to provide a mechanism for trapping analytes of interest. During an adsorption phase, a sample containing analytes of interest is introduced into the analyte trap and analytes of interest are adsorbed into the stationary phase. During a desorption phase, a carrier gas is employed for carrying desorbed analytes of interest into an attached analytical instrument. The analyte trap may be cooled during an adsorption phase such that analytes of interest are more readily adsorbed into the stationary phase coating. The analyte trap may be heated during the desorption phase to increase the rate at which the analytes of interest are desorbed from the stationary phase. A peltier thermoelectric device may be employed for such cooling and heating.

A plurality of ports are employed in combination with valves to regulate the introduction of the sample into the analyte trap and to regulate the introduction of carrier gas to aspirate analytes of interest from the flow channel.

The trap may be employed individually, or cascaded for class separations of compounds. Microdetectors placed on or between the wafers provide a feedback signal as corresponding to the composition the analytes currently flowing through the analyte trap, wherein, based on the feedback signal, some analytes of interest are directed into the GC and others to waste.

The present invention may also be adapted in certain embodiments to provide methods and apparatus whereby a plurality of analyte traps are cascaded to provide for class separation of analytes.

An analyte trap in accordance with the invention may be constructed out of silicon wafers, metallic wafers that are diffusion bonded together or other material that provides for a sealed flow chamber and a surface that will accept a bonded stationary phase.

Other aspects and advantages of the present invention will be come apparent from the following detailed description, taken in conjunction with the accompanying drawings, illustrating by way of example the principles of the invention.

DETAILED DESCRIPTION OF THE PREFERRED EMBODIMENTS

Figure 1:
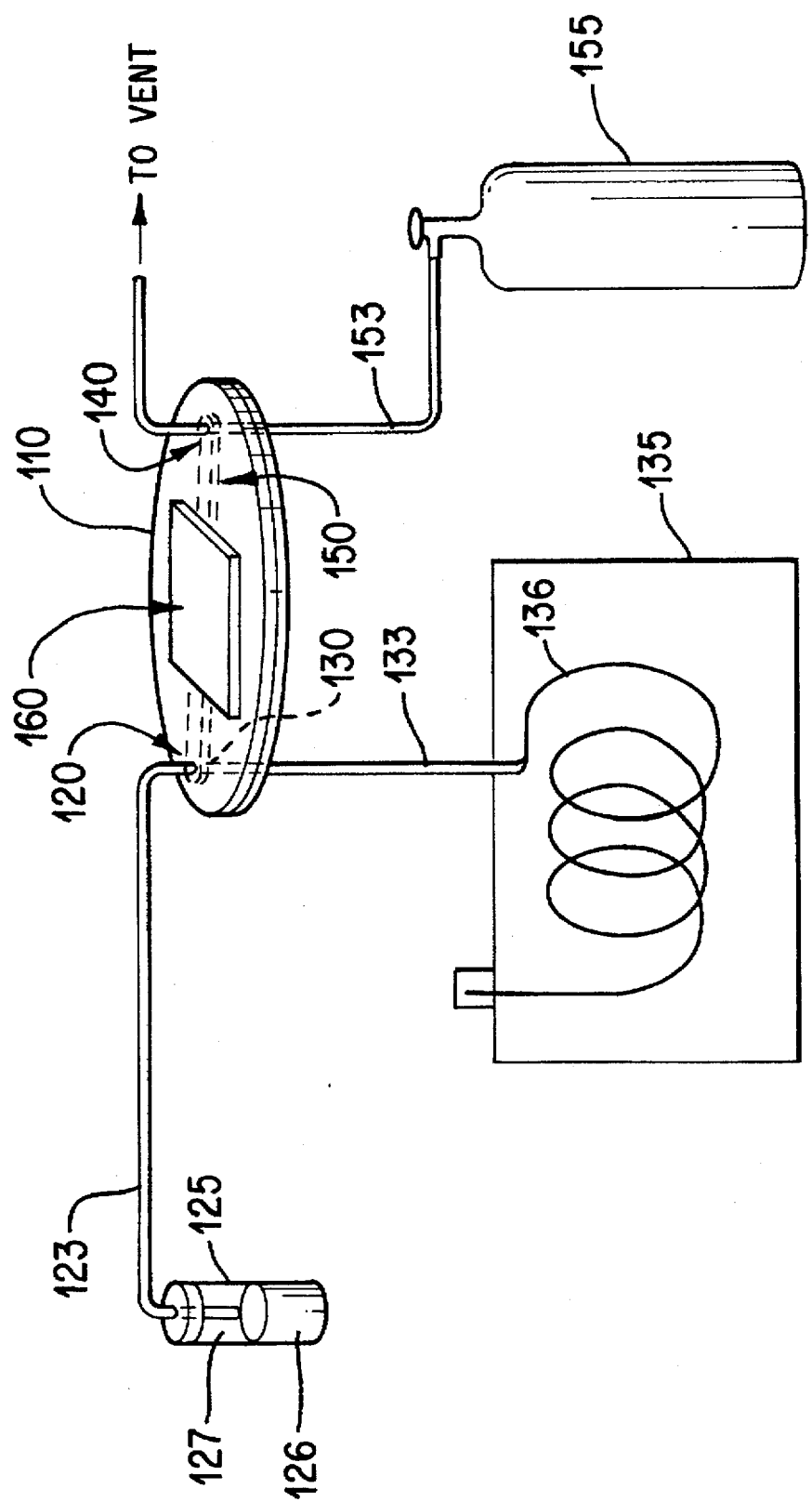
FIG. 1 is a simplified schematic representation of an analytical system employing an analyte trap for collecting analytes of interest.

With reference now to the drawings wherein like reference numerals designate corresponding parts throughout the several views, FIG. 1 illustrates a plan view of an analytical system utilizing an analyte trap 110 in accordance with the invention. The analyte trap 110 has a inlet port 120 coupled by a sample supply line 123 to a vial 125 containing a sample 126 that generates a headspace 127 above the surface of the sample 126. An analyte outlet port 130 is employed for outputting analyte to a gas chromatograph 135 via trap outlet line 133. A chromatographic column 136, within the gas chromatograph is employed for separation of the analyte of interest. While a relatively large, laboratory bench based gas chromatograph is illustrated, the invention is also comparable with a micromachined gas chromatograph as dislcosed in U.S. Pat. No. 4,474,889 entitled "Miniature Gas Chromatograph Apparatus" and U.S. Pat. No. 4,935,040 entitled "Miniature Devices Useful for Gas Chromatography" the disclosures of which are both hereby incorporated by reference. Both of these references illustrate processes for manufacturing devices from micromachined wafers.

The invention employs a vent port 140 for venting off excess headspace 127 from the vial 125 that is not adsorbed in the analyte trap 110. A source of carrier gas 155 is coupled to a carrier inlet port 150 over a carrier gas supply line 153 and is employed for carrying the analytes of interest through the capillary column 136 upon desorption. For more precise control and operating efficiency, a peltier thermoelectric device 160 may be employed for cooling the trap 110 during the adsorption phase and for heating the trap 110 during the desorption phase.

Figure 2:
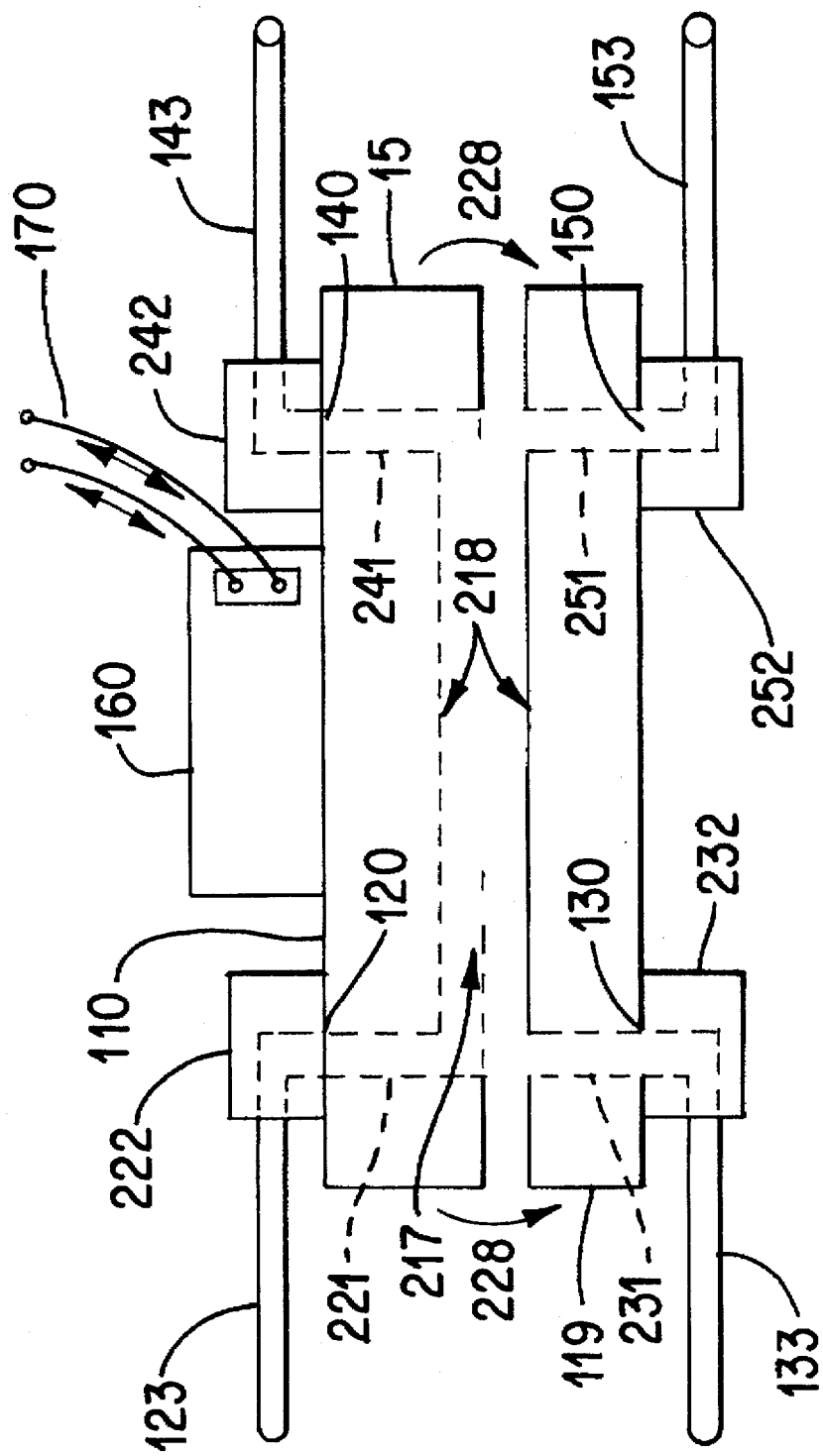
FIG. 2 depicts an exploded view of an analyte trap depicted in FIG. 1.

An exploded plan view of the analyte trap 110 is shown in FIG. 2. A top silicon wafer 115 is etched so to form a flow channel 217 when the top silicon wafer 115 is mated with a lower silicon wafer 119. After the wafers are properly mated (as suggested by the arrows 228) and secured, a stationary phase coating 218 is applied to the walls of the flow channel using techniques well known for coating gas chromatography capillary columns. A sample inlet port 120 provides access to the flow channel 217 through an inlet via 221. An inlet valve 222 is coupled to the wafer 115 adjacent to the inlet port 120 and may be actuated so as to allow the flow of a sample from a sample supply line 123 through the inlet valve 222 and into the flow channel 217. A vent port 140 is formed on the top wafer 115 and coupled to the inlet port 120 through a vent via 241 and the flow channel 217. A vent valve 242 provides for opening and closing the vent port 140 to a vent 243.

The bottom wafer 119 includes an analyte outlet port 130 opposite the inlet port 120. The outlet port 130 is coupled to the flow channel 217 through an outlet via 231. An outlet valve 232 is coupled to the bottom wafer 119 at the outlet port 130 for regulating the flow of the analyte from the flow channel 217 to a trap outlet line 133. The trap outlet line 133 is coupled to the separation column of a gas chromatograph 135 (FIG. 1). A carrier inlet port 150 is formed on bottom wafer 119 and coupled to outlet port 130 through a carrier inlet via 251 and the flow channel 217. A carrier inlet valve 252, mounted adjacent to the carrier inlet port 150 provides for the regulation of a carrier gas through the flow channel 217. A peltier thermoelectric device 160 is mounted on to the top of wafer 115 and adjacent to the flow channel 217 to provide for rapid solid-state heating and cooling of the analyte trap. While the preferred embodiment employs a peltier thermoelectric device 160, such a device is not required. The stationary phase coating is capable of adsorbing analytes of interest particularly those of low volatility, without cooling. Additionally, it would also be possible to use known cryogenic cooling devices (for example, by expansion of the carrier gas on the outside of the analyte trap) and resistance heaters to effect cooling and heating.

The analyte collection phase begins by flowing a gas stream containing analyte of interest from a source (for example, the headspace of a closed container containing a sample or the output of a supercritical fluid extraction device), to the analyte trap 110. The gas stream flows into inlet port 120, through the flow channel 217 and out the vent port 140. Current may be applied to the conduits 270 in a first direction to the peltier thermoelectric device 160 to cool the flow channel 217 for cryotrapping analytes of interest on the stationary phase coating 218.

The analyte desorption phase, in which analytes of interest are backflushed out of the analyte trap, begins by closing the inlet port valve 222 and the vent port valve 242, and opening the outlet port valve 232 and the carrier inlet port valve 252. Current may be applied to the peltier thermoelectric device in a direction opposite to that employed in the adsorption phase, so as to heat the flow channel and desorb the analytes of interest off of the stationary phase coating 218. Carrier gas 155 (FIG. 1) is directed through the carrier gas inlet port 150 to sweep the desorbed analytes of interest from the flow channel 217 and out the trap outlet port 130 for introduction onto the head of a capillary column located within the gas chromatograph 135.

Figure 3:
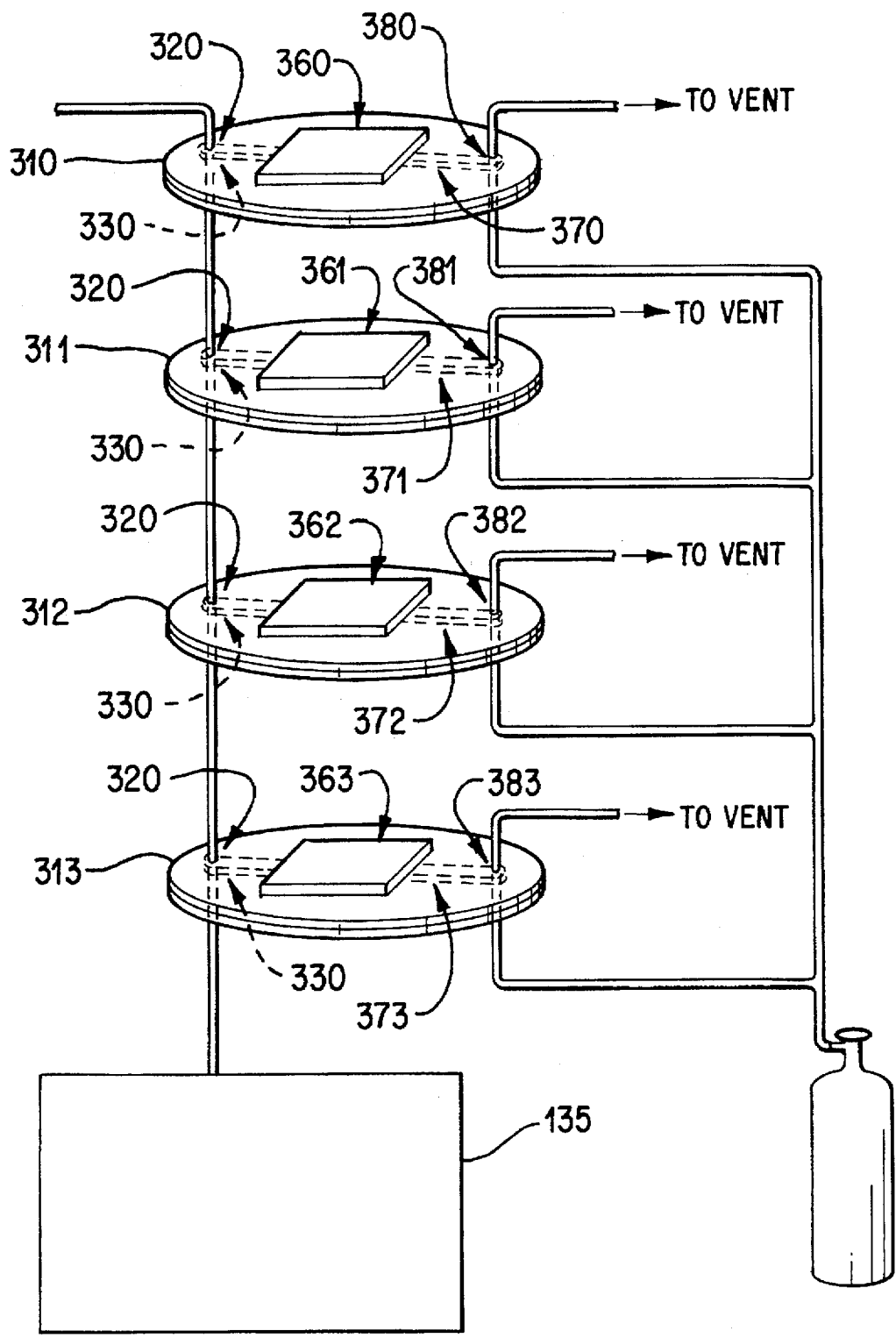
FIG. 3 depicts a series of four analyte traps as disclosed in FIG. 2 that have been cascaded together for class separations.

FIG. 3 illustrates an alternative embodiment in which a series of analyte traps are cascaded together to provide for class separations of compounds. In particular, the trap outlet port 330 of a first trap 310, is coupled to the inlet port 320 of a second trap 311. Similar connections are made to a third trap 312 and a fourth trap 313. Peltier thermoelectric devices 360, 361, 362 and 363 are each maintained at different temperatures such that different classes of analytes of interest are adsorbed into each of the analyte traps 310, 311, 312 and 313 respectfully. Alternatively, different stationary phase coatings 370, 371, 372 and 373 may be employed in each flow channel 380, 381, 382 and 383 respectfully, to trap similarly cascaded traps held at the same or at different temperatures.

While micromachined silicon wafers are employed in the preferred embodiment, an alternative embodiment may employ etched or stamped metal wafers mated and bonded through known diffusion bonding, anodic bonding or surface treatment (i.e. glueing) processes.

Figure 4:
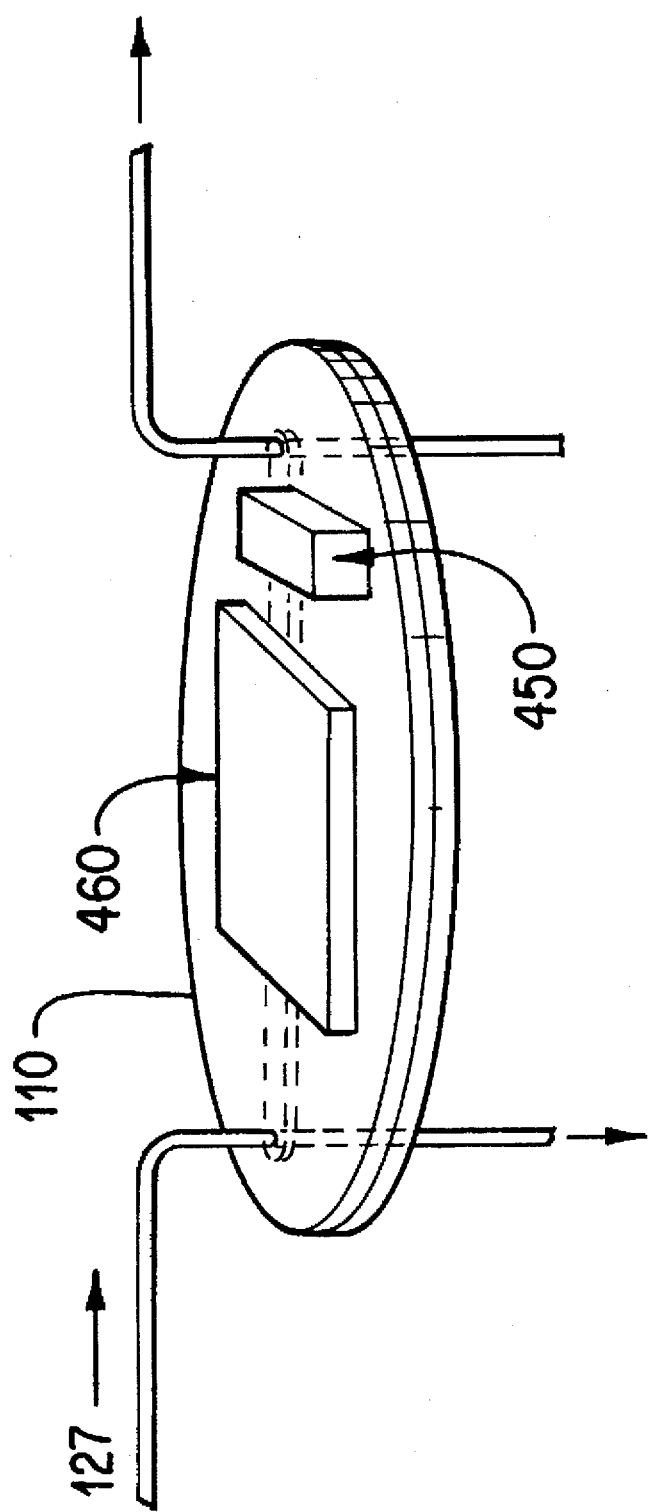
FIG. 4. depicts an analyte trap that includes a detector for providing a feedback signal during trapping.

FIG. 4 illustrates another embodiment in which a detector 450 is mounted on the analyte trap 110 so as to analyze the headspace 127 of the sample passing through the analyte trap 110. The detector 450 generates a control signal 460 that is employed for opening and closing port valves (not shown) with effecting the analytical procedure known as "heart-cutting" or "Dean switching", wherein, only a portion of the analyte desorbed off of the trap is directed to the gas chromatograph for analysis. In particular, the detector generates a feedback signal based on the analytes currently flowing through the flow channel. In response to the feedback signal, heart cutting is effected by first closing the trap outlet valve (and opening the vent valve) during the first portion of the desorption phase, then opening the trap outlet valve (and closing the vent valve) when analytes of interest are being desorbed, and finally closing the trap outlet valve (and opening the vent valve) during the last portion of the desorption phase to ensure that those analytes having relatively low volatility are not directed onto the column of the gas chromatograph for analysis.

As illustrated in FIG. 3, the invention advantageously provides for cascading multiple traps to provide for a plurality of sample preparations.

Another advantage of the invention is the ability to perform non-liquid solvent extraction of analytes of interest from a sample.

While the invention has been described and illustrated with reference to specific embodiments employing micromachined silicon, those skilled in the art will recognize that modification and variations may be made with other materials such as metal in which a trough or groove is photochemically machined or stamped in one wafer and enclosed by diffusion bonding or brazing another wafer on top (alternatively, a channel could be cut completely through one layer and cover layers could be bonded to both sides).

What is claimed is:

1. An analyte trap for introducing analytes of interest in a sample gas stream onto a column maintained at a first temperature, comprising:

a first wafer having a flow channel formed on its bottom side;

a second wafer, bonded to the bottom side of the first wafer to enclose the flow channel;

a stationary phase coating chemically bonded to the walls of the flow channel;

a plurality of ports for introducing and aspirating a sample into and out of the flow channel, the plurality of ports further comprising:

an inlet port having an inlet valve, and a vent port having a vent valve, disposed on the first wafer at opposite ends of the flow channel;

an outlet port having an outlet valve, and a carrier port having a carrier valve, disposed on the second wafer at opposite ends of the flow channel, the outlet port connected to the column, the plurality of valves for opening and closing the plurality of ports in response to a control signal;

means for cooling the analyte trap to a second temperature, whereby analytes of interest entering the inlet port in the sample gas stream are adsorbed onto the stationary phase coating during an adsorption phase before the gas stream exits the vent port; and means for heating the analyte trap to a third temperature, whereby analytes of interest are desorbed out of the stationary phase coating and flowed out the outlet port and onto the column during a desorption phase.

2. The analyte trap as claimed in claim 1, wherein the inlet valve and the vent valve are opened, and the outlet valve and the carrier valve are closed during the adsorption phase.

3. The analyte trap as claimed in claim 1, wherein the inlet valve and the vent valve are closed, and the outlet valve and the carrier valve are opened during the desorption phase.

4. The analyte trap as claimed in claim 1, the means for heating and cooling further comprising a peltier thermoelectric device, wherein current flowing in a first direction causes the device to cool, and current flowing in a direction opposite to the first direction, causes the device to heat up.

5. The analyte trap as claimed in claim 1, wherein the first and second wafer are made of micromachined silicon.

6. The analyte trap as claimed in claim 1, wherein the first and second wafers are made of metal and wherein the flow channel is stamped.

7. The analyte trap as claimed in claim 1, further comprising a detector mounted on the trap having means selectively responsive to the analytes passing through the flow channel for generating the control signal, whereby the plurality of valves are switched to flow only a portion of the analytes of interest out the outlet port.

* * * * *